United States Patent
Ohtsuki et al.

[11] Patent Number: 5,807,426
[45] Date of Patent: Sep. 15, 1998

[54] GAS CHROMATOGRAPHY APPARATUS WITH TEMPERATURE CONTROLLED CHAMBER

[75] Inventors: Satoshi Ohtsuki; Tsutomu Oie, both of Miyanohigashi-machi, Japan

[73] Assignee: Horiba, Ltd., Kyoto, Japan

[21] Appl. No.: 752,640

[22] Filed: Nov. 19, 1996

[30] Foreign Application Priority Data

Nov. 24, 1995 [JP] Japan ................................. 7-329831
Jan. 11, 1996 [JP] Japan ................................. 8-021934

[51] Int. Cl.$^6$ ............................................... B01D 15/08
[52] U.S. Cl. ........................... 96/102; 73/23.25; 95/87
[58] Field of Search ........................... 73/23.35, 23.25, 73/23.37; 95/87; 96/101–103

[56] References Cited

U.S. PATENT DOCUMENTS

| | | | |
|---|---|---|---|
| 3,165,147 | 1/1965 | Roof et al. | 96/102 X |
| 3,305,000 | 2/1967 | Bullen et al. | 96/102 X |
| 3,422,603 | 1/1969 | Redmond, Jr. | 96/103 |
| 4,070,169 | 1/1978 | Iwao et al. | 96/101 |
| 4,088,458 | 5/1978 | Jourdan | 96/102 |
| 4,580,036 | 4/1986 | Hunt et al. | 96/101 X |
| 4,599,169 | 7/1986 | Ray | 96/101 X |
| 4,771,628 | 9/1988 | Sisti et al. | 96/101 X |
| 4,948,389 | 8/1990 | Klein et al. | 95/87 X |
| 5,634,961 | 6/1997 | Gordon | 95/87 X |
| 5,656,170 | 8/1997 | Henderson | 95/87 X |

FOREIGN PATENT DOCUMENTS

| | | | |
|---|---|---|---|
| 1181448 | 11/1964 | Germany | 96/101 |
| 2921358 | 12/1980 | Germany | 96/102 |
| 0919208 | 2/1963 | United Kingdom | 96/101 |
| WO82/01662 | 5/1982 | WIPO | 96/101 |

Primary Examiner—Robert Spitzer
Attorney, Agent, or Firm—Price, Gess & Ubell

[57] ABSTRACT

The present invention enables the dissipation of thermal energy from a gas chromatography chamber containing a gas chromatography sample by providing the housing in two parts so that ambient air can be bled in during a creation of thermal energy with a heater and additional ambient air can be circulated in a cooling cycle. Additionally, a heat exchanger for receiving liquid nitrogen can also be included to increase the speed in which thermal energy can be dissipated.

18 Claims, 5 Drawing Sheets

GAS CHROMATOGRAPHY APPARATUS WITH TEMPERATURE CONTROLLED CHAMBER

BACKGROUND OF THE INVENTION

1. Field of the Invention

The present invention relates to a temperature controlled chamber that facilitates the addition and removal of heat energy to a sample, for example, to a separation column in a gas chromatography apparatus.

2. Description of Related Art

Sample chambers or ovens are provided in gas chromatography apparatus to enable the rising of the temperature of the separation column through the use of a heater. The chamber is covered with an adiabatic material to assist in the rising of the temperature with the chamber interior being closed with a cover member. When heating such a closed system, the thermal capacity that can be stored or accumulated by the adiabatic material can be relatively large. Thus, when it is desired to again lower the temperature for the next measurement cycle, after the separation column has been appropriately raised to a predetermined temperature for detection purposes, additional time must be provided in order to return the chamber to the original temperature after the heater has been turned off. Thus, the heat accumulated and stored by the adiabatic material is required to be removed and this problem lowers the operation efficiency of a gas chromatic apparatus required to make repetitive measurements.

Thus, the prior art is still seeking to optimize the ability of a gas chromatography apparatus to make reliable and efficient repetitive measurements.

OBJECTS AND SUMMARY OF THE INVENTION

An object of the present invention is to provide an improved sample chamber that can apply an appropriate amount of heat energy to a sample and then after the measurement cycle is completed be brought back to a desired premeasurement temperature range.

The present invention provides a housing with an interior chamber that is lined with an adiabatic material. The chamber includes a separation column for receiving a sample, a heater for raising the temperature of the column, and a circulation fan. In one embodiment of the invention, the temperature of the separation column can be raised, while the interior of chamber is placed in an open condition for communicating with ambient air to provide ventilation of cool air to the interior of the chamber. As a result, the thermal capacity of energy to be absorbed by the adiabatic material can be lesser so that a subsequent cooling operation after the appropriate application of heat energy to the separation column has been completed, can be more efficiently carried out with the chamber being in an open condition to permit an introduction of ambient air.

An alternative embodiment of the present invention includes not only a front cover that can open and close and a chamber for supporting the separation column along with a heater for raising the temperature of the separation column, but further provides a heat exchanger for lining the chamber and adapted to receive a coolant, such as liquid nitrogen, having a low boiling point whereby evaporation of the coolant can rapidly remove the accumulated heat from the chamber.

Thus, a gas chromatography apparatus can be one application of the present invention with a separation column being provided for receiving a sample within a chamber of a housing member. A detector for measuring the sample is also provided with the improvement involving controlling the thermal application of energy to and from the separation column member. The housing member can be bifurcated into a first portion and a second portion that are relatively movable to increase an opening to the ambient air. A source of heat energy can be applied to the interior of the housing member, for example, through a heater unit and a fan. The first portion can house the chamber for the separation column, and the second portion can be a movable cover member, with the cover member driven, for example, by an air cylinder, solenoid, electric motor, etc. to control the position of the first and second portion to thereby permit heat energy to be removed from the separation column and the interior of the chamber by increasing the flow of ambient air. Alternatively, a coolant and a heat exchanger can also be applied to the interior of the chamber to further facilitate the removal of the thermal energy.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved gas chromatography apparatus with a temperature controlled chamber.

Figure 1:
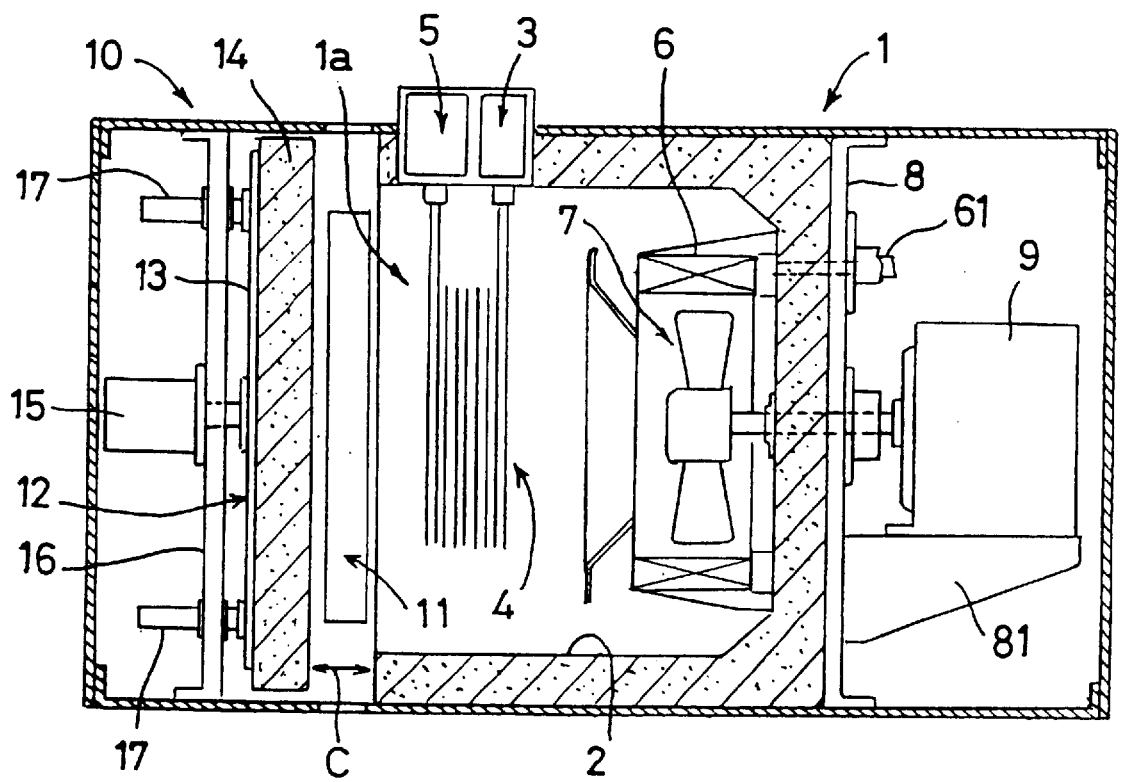
FIG. 1 is a cross-sectional view showing one embodiment of a chamber to facilitate an application of removal of thermal energy to a separation chamber.

Referring to FIG. 1, the housing member 1 of the present invention is disclosed in a schematic cross-sectional view. In this embodiment, the housing member 1 provides a chamber for use in a gas chromatography apparatus. Since people skilled in gas chromatography are aware of the components of such a machine, a description of the same will be omitted and only those components relevant to the present invention will be described.

A separation column 4 or sample cell is schematically disclosed with a sample pouring opening 3 being provided at the top of the housing member 1 and the interior chamber of the housing member being covered with adiabatic material 2. A detector member 5 is provided for measurement of a separation column. The housing member 1 is divided into a first portion which supports the separation column 4, and a second portion that includes a movable cover body portion 10 that is integrated into the left side of the housing member 1. The cover body portion 10 can be relatively movable and in FIG. 1 is disclosed in an open condition with vent openings being provided about the cover body portion 10, as shown in the top, bottom, and ventilation opening 11 on the side. Mounted within the cover body portion 10 is a movable cover body 12 capable of moving in the direction of the arrow C for opening and closing an opening 1a of the first portion. A drive unit 15, such as a pneumatic air cylinder and piston, or alternatively a solenoid, electric motor, etc., can be used to drive the movable cover body member 12 with a pair of guide rods 17 connected to a cover plate 13 and journaled in appropriate holes within the support plate 16 guide the movable cover body 12. Adiabatic material 14 can line internally the cover plate 13 with, as shown in FIG. 1, an air cylinder 15 mounted on the support plate 16 to control the positions of the movable cover body portion 10.

Mounted within the chamber in close approximation to the separation column 4 is a heater 6 that is capable of raising the temperature of the separation column 4. The heater 6, in the preferred embodiment, can be electrical with the wiring 61 extending through the compartment wall 8. The heater 6 can extend about a fan 7 that is also journaled within the adiabatic material 2 and through the compartment wall 8 to be driven by a motor 9. A support member 81 can mount to the compartment wall 8 and support the motor 9 in a cantilevered manner. An appropriate cowling is disclosed for distributing the heated air from the fan 7 to the separation column 4.

Figure 2A:
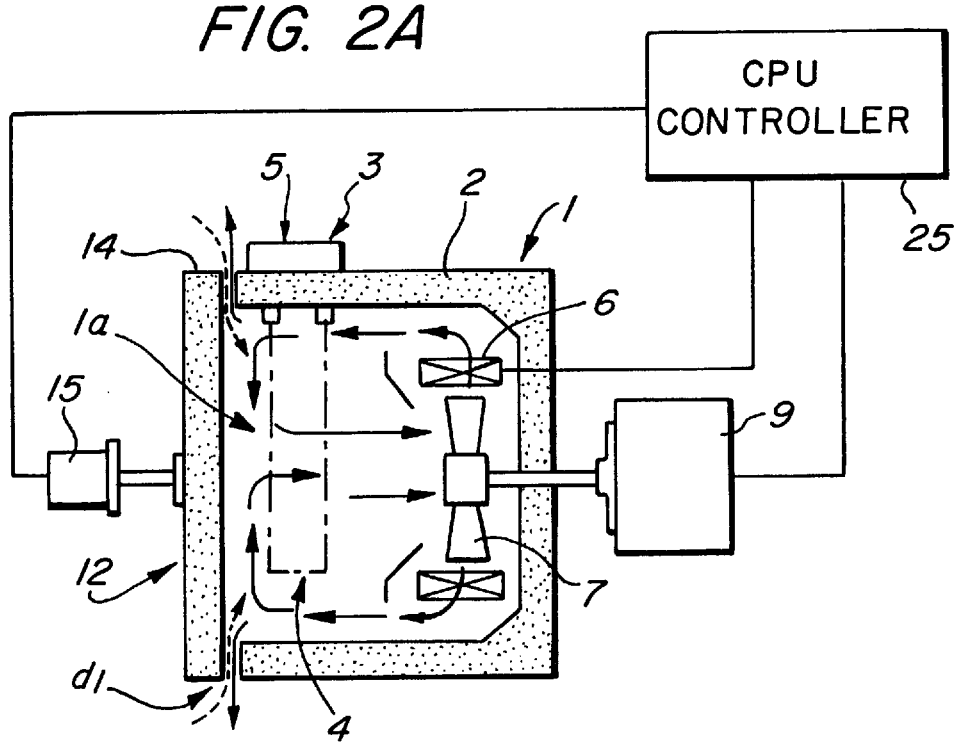
FIG. 2A is a schematic illustration disclosing the application of heat energy to the chamber.

Referring to FIG. 2A, the air cylinder 15 can be moved to set a small clearance $d_1$ automatically through, for example, a CPU controller 25. The CPU controller 25 can also energize the heater 6 and the fan 7 so that air circulated by the fan 7 will both permit air to be bled into the inside of the chamber and permit the egress of air from the chamber during the application of thermal energy to the separation column 4. By this arrangement, the separation column 4 will be raised to the appropriate temperature evenly by the fan 7, while the quantity of thermal energy accumulated by the adiabatic material 2 and 14 can be controlled to be at a lower amount, because the temperature rising of the separation column 4 is carried out through the introduction of ambient air. Thus, while the efficiency of the heater 6 may be lessened by the addition of ambient air and the loss of heated air through the clearance $d_1$, the purpose of lessening heat accumulated in the walls of the chamber is achieved.

Figure 2B:
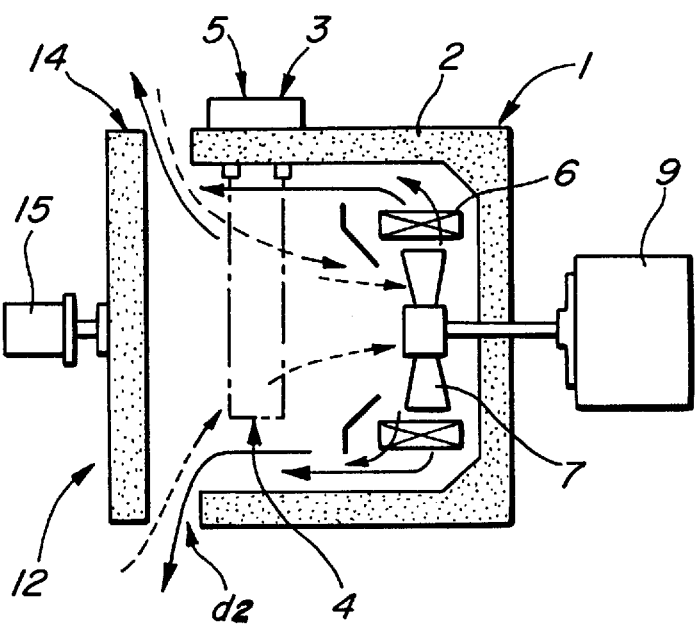
FIG. 2B is a schematic illustration disclosing the removal of thermal energy from the separation chamber.

FIG. 2B is a schematic representation of returning the chamber and the separation column to the desired premeasurement temperature. In this regard, the air cylinder 15 is activated to increase the opening between the cover body 12, constituting the second portion of the housing member, and the chamber constituting the first portion of the housing member. With the heater 6 shut off and the fan 7 activated, a clearance distance of $d_2$ exists between the cover body 12 and the opening 1a, so that there is a sufficient opening that the thermal capacity that is accumulated in the adiabatic materials 2 and 14, can be adequately released during the cooling mode of operation to expedite the next measurement cycle.

Since the temperature is adapted to be adjusted by the heat balance between the temperature of the air coming and going under an open condition in communication with the ambient air, while the heater 6 provides a thermal input of energy, it is possible to raise the temperature of the separation column 4 relatively independent of the temperature effect by the adiabatic materials 2 and 14 so that the resulting cycle of lowering the temperature can be significantly shorter. As a result, an analysis cycle time in a continuous measurement mode can be significantly shortened to increase the number of measurements with high efficiency.

As can be appreciated, open air can be inserted into the housing member 1 through the location of an appropriately sized hole provided at a proper location in the housing 1 instead of a provision of a clearance between the cover body 12 and the opening 1a. Adjustment of the hole diameter can be used to provide a proper formation of clearance for introduction of the open air. Thus, a ventilation unit with a controlled opening to permit the fan to draw air in and to exhaust air is provided.

Figure 3:
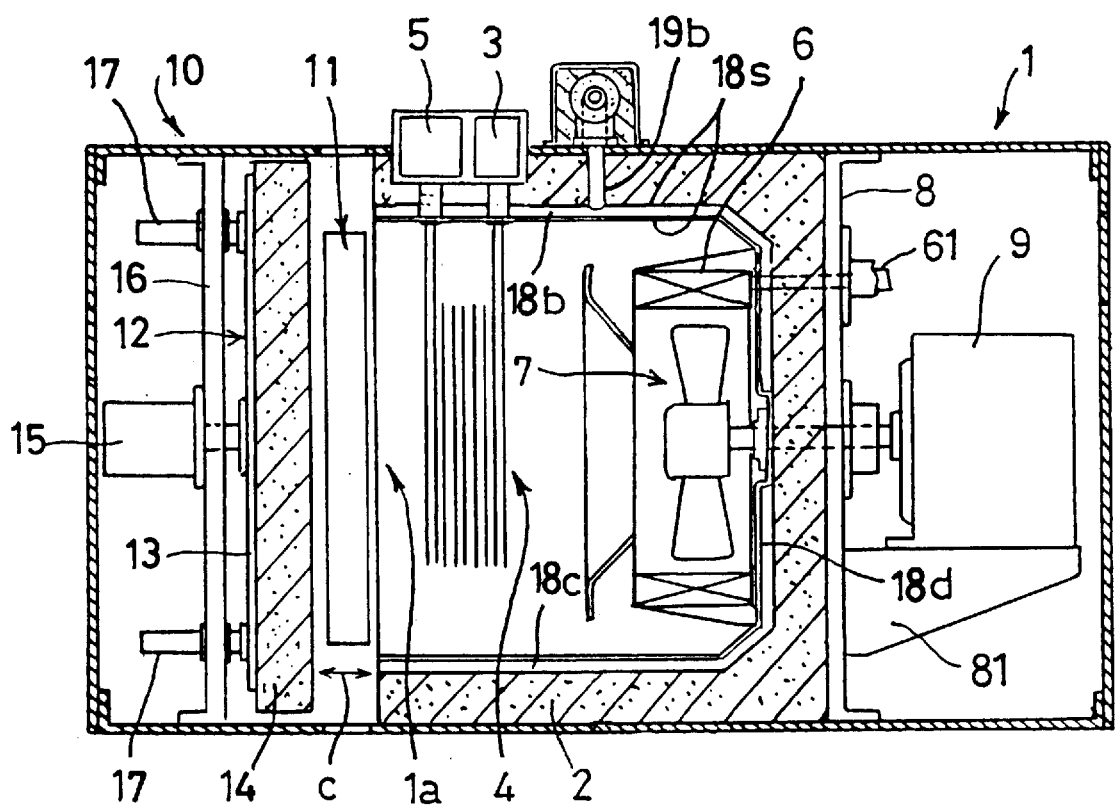
FIG. 3 is a cross-sectional view showing a second embodiment of the present invention.
Figure 4:
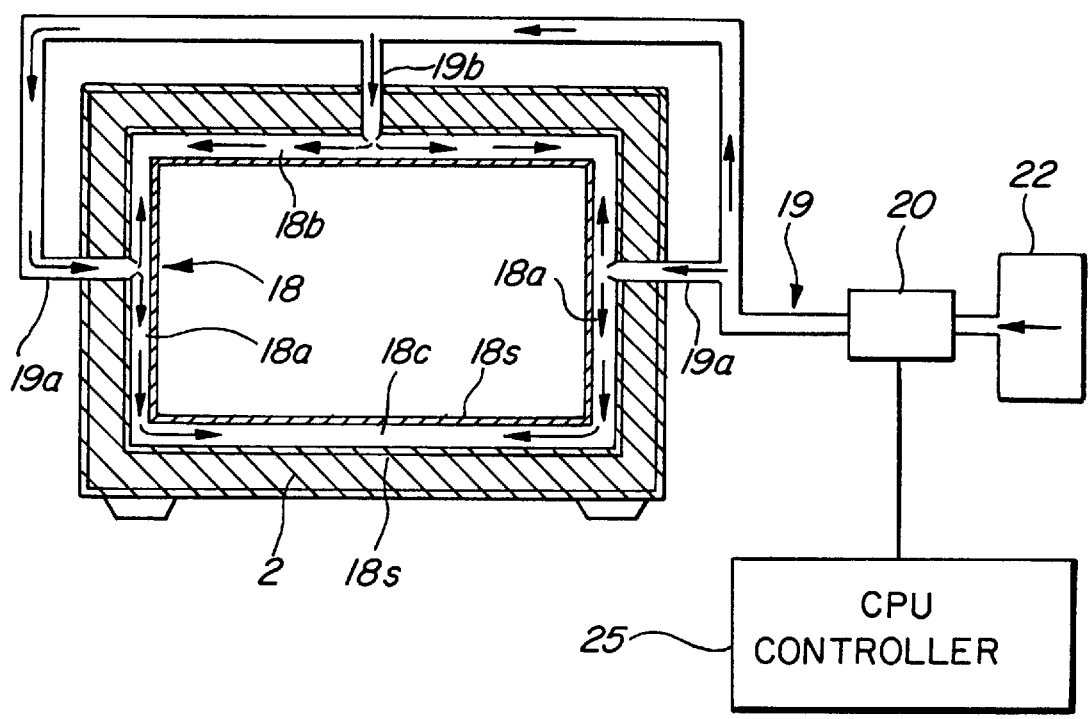
FIG. 4 is a schematic transverse view disclosing the heat exchanger of the second embodiment.

FIG. 3 is a cross-sectional schematic view of an alternative embodiment of the present invention that further incorporates a heat exchanger to enable a rapid dissipation of any thermal energy that is accumulated in the chamber. Thus, in FIG. 3, the cover body 12 is in an open position, and the interior surface of the chamber is lined with a heat exchanger 18 that is collectively made from, for example, a series of two-ply heat resistant metal plate members, e.g. stainless steel plates 18s. To form the heat exchanger, both side portions 18a, 18a, a ceiling face portion 18b, a bottom face portion 18c, and a rear face portion 18d provide a narrow clearance of approximately 2 to 3 mm in size, as can be seen in FIG. 4. This can be compared with the thickness of the adiabatic material 2, which is approximately 30 mm thick.

As can be further seen in the schematic view of FIG. 4, a source of liquid nitrogen, $N_2$, such as a cylinder 22, can be connected through a solenoid valve 20 to a duct system 19 that communicates with the inside of the heat exchanger 18 through a series of ducts 19a, 19b. These ducts can introduce a liquid nitrogen which has a boiling point of a −196 degrees C. as the coolant or refrigeration medium to ensure a rapid removal of thermal energy from the chamber. The clearance of the refrigerating space within the heat exchanger 18 is approximately 2–3 mm and the outer diameter/inner diameter of the ducts 19a, 19b are, for example, 6 mm/4 mm.

Figure 5A:
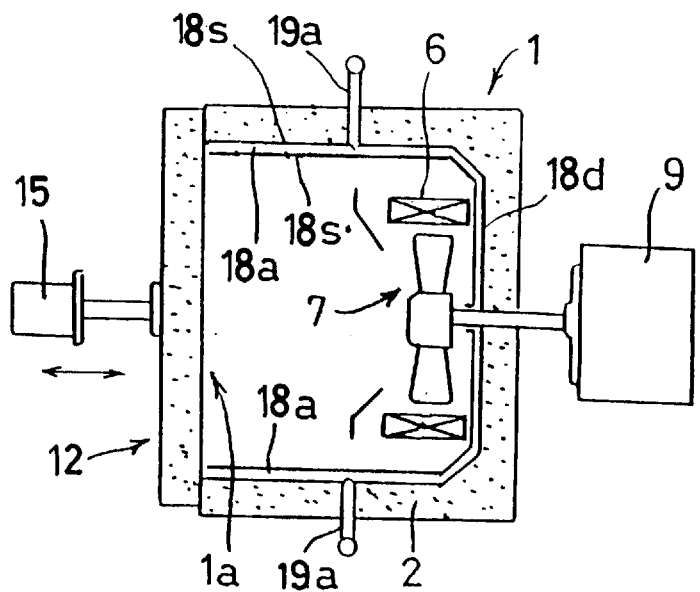
FIG. 5A is a schematic illustrative view disclosing the second embodiment with thermal energy being applied to the chamber.
Figure 5B:
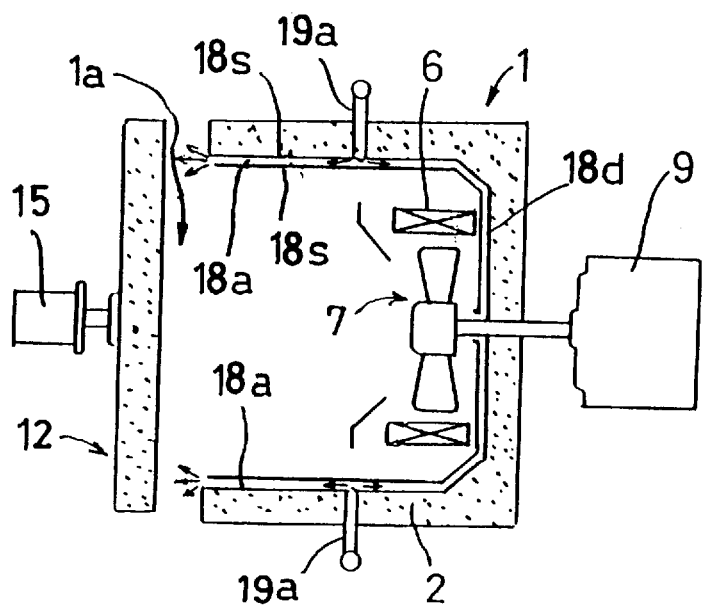
FIG. 5B is a schematic illustrative view disclosing the second embodiment with thermal energy being removed from the chamber.

Referring to FIG. 5a, the temperature of the separation column 4 is raised within the housing 1 with the cover body 12 closed to thereby conserve the heat 6 during the rotation of the fan 7. After the analysis has been conducted at a desired temperature, the cover body 12 can be open, as shown in FIG. 3 and in FIG. 5B, and the solenoid valve 20 can be opened for filling the liquid nitrogen into the heat exchanger 18. This can occur in approximately five seconds at one half of an atmospheric pressure and can also be automatically controlled by the controller 25.

When the liquid nitrogen is adequately filled into the heat exchanger 18, the liquid nitrogen will evaporate and withdraw the accumulated thermal energy in the adiabatic material 2 and the metal plates of the heat exchanger. Thus, by utilizing an evaporation phenomena of the liquid nitrogen resulting from the accompanying phase change, a rapid absorption of thermal energy can occur. Since the nitrogen is inert and the heat exchanger has a narrow clearance, there is no requirement for a special discharge or recovering device and the nitrogen can be rapidly discharged externally through the front opening.

In this embodiment of the invention, the utilization of the heat exchanger 18 and the evaporation of the nitrogen gas can considerably shorten the time required for the temperature analysis of a sample in a separation column 4. Thus, even if the constant temperature analysis is to take place initially at a room temperature, the second embodiment of the invention can quickly accommodate the dissipation of the accumulated thermal energy to shorten the measurement cycle time. Additionally, the activation of the fan 7 and the opening of the cover body 12 enables ambient air to also rapidly circulate through the chamber to remove thermal energy from the adiabatic material.

As can be appreciated, a ROM can store appropriate predetermined drive signals to enable the controller 25 to automatically provide a measurement cycle. Additionally, temperature sensors (not shown) can monitor temperatures for the controller 25.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

We claim:

1. In a gas chromatography apparatus having a separation column member for receiving a sample and a detector for measuring the sample, the improvement of controlling thermal application of energy to and from the separation column member comprising:

a housing member having a chamber for supporting the separation column member with one side of the chamber forming a movable cover that is relatively movable to increase an opening to the ambient air;

means for providing a source of heat energy to an interior of the housing member;

means for removing heat energy from the separation column member including means for controlling the position of the movable cover to a first position where a small opening is only provided between the cover member and the chamber and the remainder of the chamber remains closed to control the application of heat energy to the separation column member and to a second position where a larger opening is only provided between the cover member and the chamber and the remainder of the chamber remains closed to enable a rapid removal of heat energy from the separation column member.

2. The invention of claim 1 wherein the means for removing heat energy further includes the housing member and a heat exchanger extending about the interior of the housing member and means for applying a coolant to the heat exchanger.

3. The invention of claim 1 wherein the means for providing a source of heat energy further includes a heater unit with the housing member.

4. The invention of claim 1 further including a fan member within the housing member.

5. The invention of claim 1 wherein the means for controlling includes a control member for relatively moving the movable cover.

6. The invention of claim 5 wherein the control member is an one of an air cylinder, a solenoid, or an electric motor.

7. The invention of claim 6 wherein the means for removing heat energy further includes a heat exchanger unit within the housing member and applying means for applying a coolant to the heat exchanger unit, the movable cover further controlling an opening for the heat exchanger to the ambient air whereby the coolant can be released to evaporate and accelerate the removal of heat energy from the housing member.

8. The invention of claim 7 wherein the heat exchanger unit approximately covers the interior of the chamber.

9. The invention of claim 7 further including a source of nitrogen gas as the coolant connected to the applying means.

10. A testing apparatus for applying heat to a sample in a gas chromatography apparatus comprising:

a housing member having a chamber with a plurality of side walls with one of said side walls of the chamber forming a movable cover that is relatively movable to increase an opening to the ambient air;

a sample cell for holding the sample to be tested mounted within the housing member;

means for providing a source of heat energy to an interior of the housing member to heat the sample;

means for removing heat energy from the sample cell including a heat exchanger for substantially covering a plurality of said side walls of the chamber; and means for controlling the position of the movable cover to a first position to control the application of heat energy to the sample cell and to a second position to enable a rapid removal of heat energy from the sample cell.

11. The invention of claim 10 further including means for applying a coolant to the heat exchanger.

12. The invention of claim 11 further including a heater unit within the housing member.

13. The invention of claim 12 further including a fan member within the housing member.

14. The invention of claim 12 further including a source of nitrogen gas as a coolant connected to the heat exchanger.

15. In a gas chromatography apparatus having a separation column member for receiving a sample and a detector for measuring the sample, the improvement of controlling thermal application of energy to and from the separation column member comprising:

a housing member having a chamber with a plurality of side walls for supporting the separation column member with one side wall of the chamber forming a movable cover that is relatively moveable to increase an opening to the ambient air, the remaining side walls having metallic plates that extend across the side walls and form a heat exchanger member that substantially encloses the chamber;

means for applying heat energy to the chamber; and means for providing a coolant to the heat exchanger member.

16. The invention of claim 15, further including a ventilation unit having a fan unit, and drive means for driving the movable cover relative to the housing member.

17. The invention of claim 16 further including a controller member for controlling the activation of the fan unit, the heat means and the movable cover to regulate the application of heat in a first mode of operation and the removal of heat from the housing member in a second mode of operation.

18. The invention of claim 15 further including means for moving the moveable cover, the heat exchanger member includes an opening that is controlled by the moveable cover.

* * * * *